United States Patent
Goettel et al.

(10) Patent No.: US 7,361,198 B2
(45) Date of Patent: Apr. 22, 2008

(54) M-DIAMINOBENZENES, THEIR ACID ADDUCTS AND THE USE THEREOF IN COLORANTS

(75) Inventors: Otto Goettel, Marly (CH); Andre Hayoz, Senedes (CH); Emmanuel Morand, Villars-sur-Glane (CH)

(73) Assignee: Wella AG, Darmstadt (DE)

( * ) Notice: Subject to any disclaimer, the term of this patent is extended or adjusted under 35 U.S.C. 154(b) by 284 days.

(21) Appl. No.: 10/542,494

(22) PCT Filed: Sep. 2, 2004

(86) PCT No.: PCT/EP2004/009794

§ 371 (c)(1),
(2), (4) Date: Jul. 15, 2005

(87) PCT Pub. No.: WO2005/051889

PCT Pub. Date: Jun. 9, 2005

(65) Prior Publication Data

US 2006/0047172 A1    Mar. 2, 2006

(51) Int. Cl.
*A61K 7/13* (2006.01)
(52) U.S. Cl. .................. 8/405; 8/406; 8/410; 8/411; 8/412
(58) Field of Classification Search .......... 8/405, 8/406, 410, 411, 412
See application file for complete search history.

(56) References Cited

U.S. PATENT DOCUMENTS 3,232,995 A    2/1966   Solodar
4,314,809 A    2/1982   Rose et al.
4,543,425 A    9/1985   Konrad et al.
5,518,507 A    5/1996   Audousser et al.
6,461,389 B1 * 10/2002  Genet et al. ................... 8/405

FOREIGN PATENT DOCUMENTS

DE    28 52 156        6/1980
DE    32 29 973 A1     2/1984

OTHER PUBLICATIONS

STIC Search Report dated May 23, 2007.*
S. Saravanan et al: "Microwave-Induced Synthesis of Nitrostilbenes Under . . . ", Synthetic Communications, 31 (6), pp. 823-826, 2001.
S.B. Lokhande et al: "Application of Phase-Transfer Catalysis to the Synthesis . . . " Indian Journal of Chemistry, vol. 25B, May 1986, pp. 485-488.
Bruce G. Tiemann et al: "Molecular and Macroscopic Second-Order Optical . . . " American Chemical Society, Chem Matter, 1990, 2, pp. 690-695.

* cited by examiner

*Primary Examiner*—Eisa Elhilo
(74) *Attorney, Agent, or Firm*—Michael J. Striker

(57) ABSTRACT

The present invention relates to novel m-diaminobenzenes of formula (I)

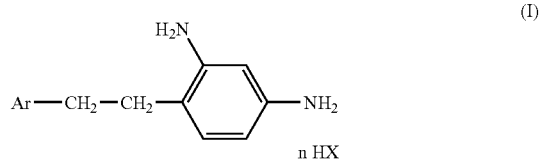

to the use thereof in colorants and to the oxidative hair colorants containing said m-diaminobenzenes.

14 Claims, No Drawings

M-DIAMINOBENZENES, THEIR ACID ADDUCTS AND THE USE THEREOF IN COLORANTS

CROSS-REFERENCES

This is the U.S. National Stage of PCT/EP 2004/009794, filed Sep. 2, 2004, in Europe, which, in turn, claims the benefit of priority of invention based on DE 103 51 842.8 filed Nov. 6, 2003 in Germany. The foregoing International and German Patent Applications disclose substantially the same invention as disclosed and claimed herein below and provide the basis for a claim of priority of invention under 35 U.S.C. 119 (a) to (d) for the invention claimed herein below.

BACKGROUND OF THE INVENTION

The invention relates to novel oxidation dye precursors and to agents for coloring keratin-containing fibers, particularly human hair, that contain these compounds.

In the field of traditional hair dyeing, oxidation dyes have attained substantial importance. The color in this case is created by reaction of certain developers with certain couplers in the presence of an oxidant. Of particular importance are hair colorants for coloring in the natural shade range. By a suitable combination of developers and couplers, trendy shades can also be attained.

Dyes intended for dyeing human hair are subject to special requirements. On the one hand, such dyes must give colorations of the desired shade and intensity and, on the other, they must be toxicologically and dermatologically harmless and non-sensitizing.

The requirements placed on dyes intended for achieving trendy color shades can be significantly different from those placed on dyes for covering the natural shade range. A primary criterion is, for example, the purity of the dye, which is reflected in the brilliance of the resulting color. In the blue range, in particular, no combinations have thus far been found which, together with the often used p-phenylenediamines [for example p-phenylenediamine, p-toluylenediamine and 2,5-diamino-(2'-hydroxyethyl)benzene] would make it possible to obtain very pure blue shades. Common blue couplers, for example 2,4-diaminophenoxyethanol, 5-[(2-hydroxyethyl)amino]-2-meth-oxyaniline or 1,3-di(2,4-diami-nophenoxy)propane, cannot produce brilliant blue shades, because they give rise to a considerable red content. In the L*a*b*color system, this red content is indicated by increased a* values.

SUMMARY OF THE INVENTION

The object therefore was to provide novel coupler compounds which—particularly in combination with the often used p-phenylenediamines—would give blue shades and afford oxidation colorants with high resistance to external influences, particularly to frequent washing and sunlight.

Surprisingly, we have now found that certain m-diaminobenzene derivatives meet the said objectives in outstanding manner. Hence, the present invention has for an object m-diaminobenzenes of formula (I)

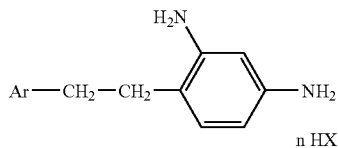

wherein
n is a numeral with $0 \leq n \leq 3$,
HX stands for an organic or inorganic acid and
Ar denotes a naphthyl group, a methylenedioxyphenyl group, a substituted or unsubstituted or benzo-condensed five- or six-member heteroaromatic group, particularly a pyridyl group, furyl group, thienyl group, pyrrol group, indolyl group, imidazolyl group or pyrazolyl group: or a benzoaromatic group of formula (II)

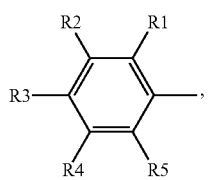

wherein the R1 to R5 groups independently of each other denote one of the following residual groups: a hydrogen atom, a halogen atom, a hydroxyl group, a nitrile group, a carboxamido group, an acetylamino group, a straight-chain or branched $C_1$-$C_{12}$-alkyl group, a straight-chain or branched $C_1$-$C_{12}$-alkoxy group, a straight-chain or branched $C_1$-$C_{12}$-alkylamino group, a straight-chain or branched di-$(C_1$-$C_6)$-alkylamino group, a phenyl group, a morpholino group, a pyrrolidino group, a piperidino group, a piperazino group, a $C_2$-$C_4$-hydroxyalkyl group, a $C_2$-$C_4$-hydroxyalkoxy group, a benzyloxy group, a trifluoromethyl group or a methylsulfonyl group.

To prepare the acid adducts, organic acids can be used besides mineral acids. Preferred acids include hydrochloric acid, sulfuric acid, phosphoric acid, citric acid and tartaric acid. Hydrochloric acid and sulfuric acid are particularly preferred.

The following compounds of the invention are especially preferred:

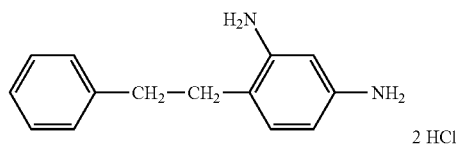

1,3-Diamino-4-(2-phenylethyl)benzene dihydrochloride (1a)

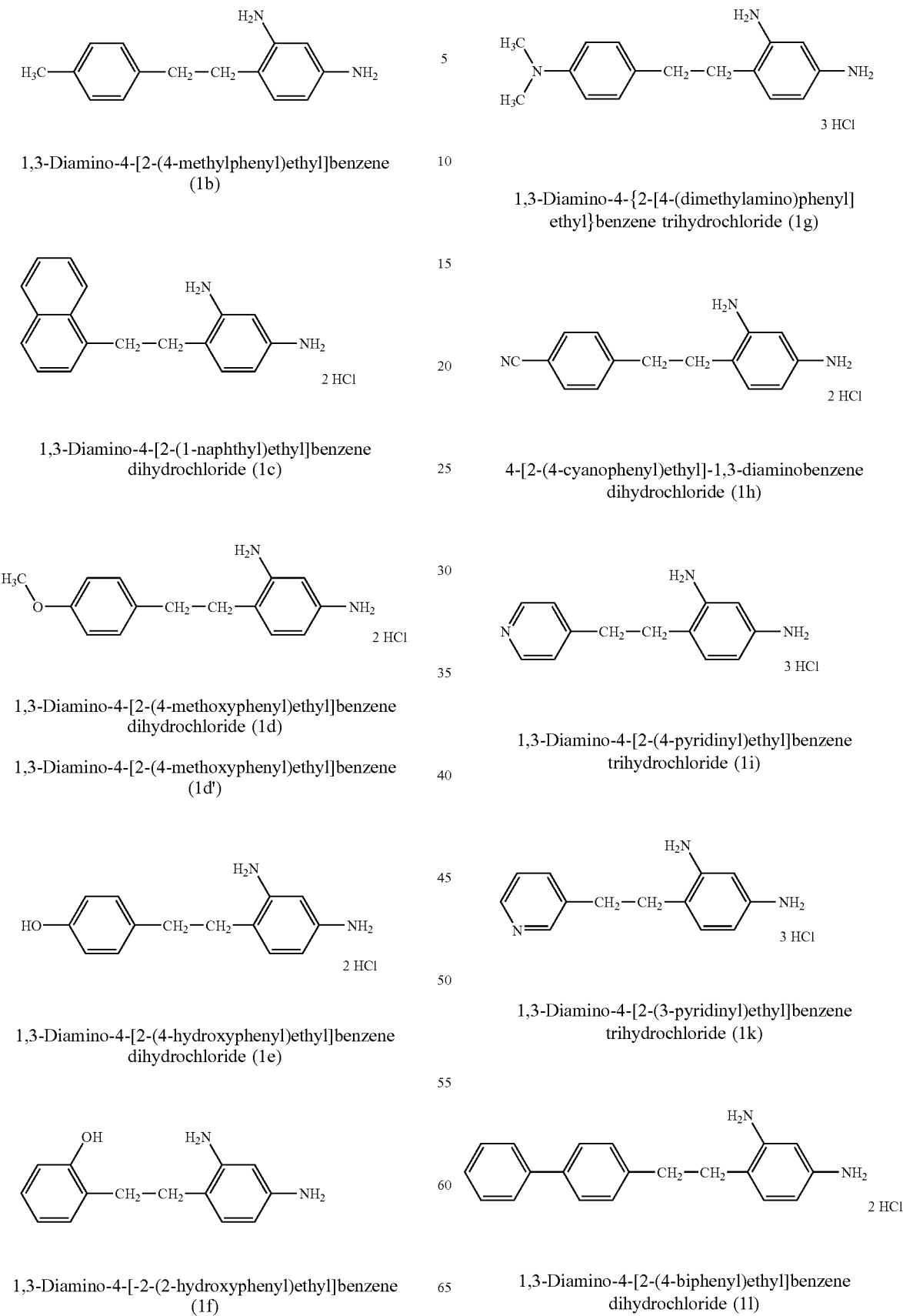

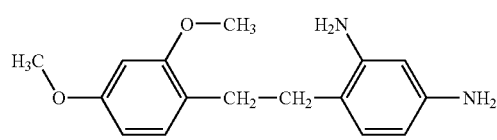

1,3-Diamino-4-[2-(2,4-dimethoxyphenyl)ethyl]benzene (1m)

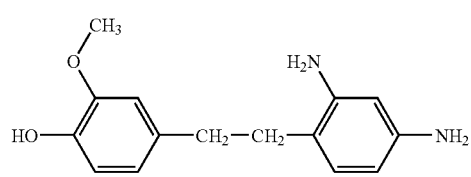

1,3-Diamino-4-[2-(4-hydroxy-3-methoxyphenyl)ethyl]benzene (1n)

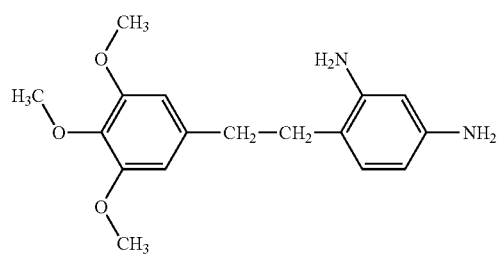

1,3-Diamino-4-[2-(3,4,5-trihydroxyphenyl)ethyl]benzene (1o)

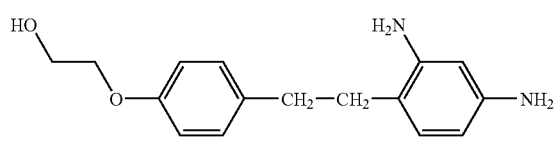

1,3-Diamino-4-{2-[4-(2-hydroxyethoxy)phenyl]ethyl}benzene (1p)

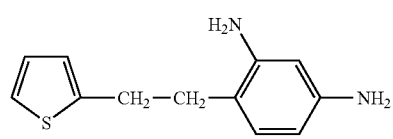

1,3-Diamino-4-[2-(2-thienyl)ethyl]benzene (1q)

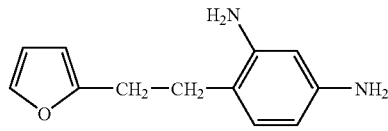

1,3-Diamino-4-[2-(2-furyl)ethyl]benzene (1r)

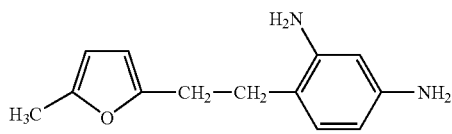

1,3-Diamino-4-[2-(5-methyl-2-furyl)ethyl]benzene (1s)

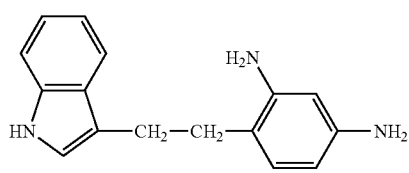

1,3-Diamino-4-[2-(1H-indol-3-yl)ethyl]benzene (1t)

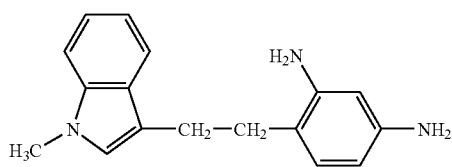

1,3-Diamino-4-[2-(1-methyl-1H-indol-3-yl)ethyl]benzene (1u)

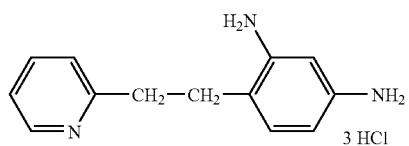

1,3-diamino-4-[2-(pyridyl)ethyl]benzene trihydrochloride (1v)

The compounds of the invention of formula (I) are preferably prepared under Knoevenagel conditions by condensation of an aldehyde of general formula (III) with 2,4-dinitrotoluene (IV) to give the stilbenes (V). For the condensation, the reader is referred to, in particular, the two literature references S. B. Lokhande, D. W. Rangnekar, Ind, J. Chem. 25B, 485-8 (1986) and B. G. Tiemann et al., Chem. Mater. 1990, 2, 690-695. Complete reduction of the nitro groups and of the stilbene double bond provides access to the m-phenylenediamines (I) which can be isolated as free bases or preferably as the acid adducts.

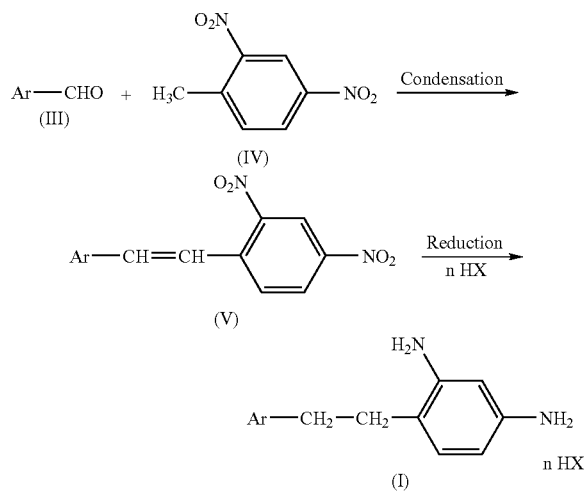

The m-diaminobenzenes of formula (I) are eminently suited as dye precursors in the oxidative system for coloring natural and synthetic fibers.

Hence, another object of the present invention is the use of m-diaminobenzenes of formula (I) for the oxidative coloring of fibers, particularly keratin fibers, for example wool or hair and particularly human hair.

A further object of the present invention is an agent for the oxidative coloring of fibers, particularly keratin fibers, for example wool or hair and particularly human hair, which in an appropriate dye carrier composition contains at least one m-diaminobenzene of formula (I).

The m-diaminobenzenes of formula (I) can be used alone or in combination with other developers and/or couplers, the quantity of the m-diaminobenzenes of formula (I) used amounting to about 0.01 to 20 weight percent and preferably 0.1 to 10 weight percent.

Developers that are eminently suited for combination with the compounds of the invention in an oxidative formulation are, for example, the para-phenylenediamine derivatives, para-aminophenol derivatives and 4,5-diaminopyrazole derivatives as well as the salts thereof.

Particularly noteworthy are the following compounds: 1,4-diaminobenzene (p-phenylenediamine), 1,4-diamino-2-methylbenzene (p-toluylenedia-mine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2-hydroxyethyl)amino]aniline, 4-[(2-methoxyethyl)-amino]aniline, 4-[(3-hydroxypropyl)amino]aniline, 1,4-diamino-2-(2-hydroxyethyl)benzene, 1,4-diamino-2-(1-methylethyl)benzene, 1,3-bis[(4-aminophenyl)-(2-hydroxyethyl)amino]-2-propanol, 1,8-bis-(2,5-diaminophenoxy)-3,6-dioxaoctane, 4-aminophenol, 4-amino-3-meth-ylphenol, 4-methylaminophenol, 4-amino-2-(aminomethyl)phenol, 4-amino-2-[(2-hydroxy-ethyl)amino]methylphenol, 4-amino-2-(meth-oxymethyl)phenol, 4-amino-2-(2-hydroxy-ethyl)phenol, 5-aminosalicylic acid, 2,5-diaminopyridine, 2,4,5,6-tet-raaminopyrimidine, 2,5,6-triamino-4-(1H)-pyrimidone, 4,5-diamino,-1-(2-hydroxyethyl)-1H-pyrazole, 4,5-diami-no-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyra-zole, 1,2-bis-(4,5-diamino-1H-pyrazol-1-yl)ethane, 1,4-bis-(4,5-diaminopyrazol-1-ylmethyl)-benzene, 4,5-diamino-1-(2-methylphenyl)-1H-pyrazole, 4,5-diamino-1-(3-methylphenyl)-1H-pyrazole, 4,5-diamino-1-(4-methylphenyl)-1H-pyrazole, 4,4-diamino-1-(2,4-dimethyl-phenyl)-1H-pyrazole, 4,5-diamino-1-(2,5-dimethylphenyl)-1H-pyrazole, 4,5-diamino-1-(2-ethylphenyl)-1H-pyrazole, 4,5-diamino-1-(4-isopropylphenyl)-1H-pyrazole, 4,5-diamino-1-(4-methoxyphenyl)-1H-pyrazole, 1-(4-aminophenyl)-4,5-diamino-1H-pyrazole, 1-(4-chloro-phenyl)-4,5-diamino-1H-pyrazole, 4,5-diamino-1-(2-pyridinyl)-1H-pyrazole, 2-aminophenol, 2-amino-6-methylphenol and 2-amino-5-methylphenol or the salts thereof.

Suitable additional couplers that can be used in combination with the compounds of the invention to achieve certain color shades are the following:

N-(3-dimethylaminophenyl)urea, 2,6-diaminopyridine, 2-amino-4-[(2-hydroxy-ethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methyl-benzene, 2,4-di[(2-hydroxyethyl)amino]-1,5-dimethoxybenzene, 2,3-diamino-6-methoxypy-ridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)-benzene, 2,4-diamino-1-(3-hydroxypropoxy)benzene, 1-(2-aminoethoxy)-2,4-diaminoben-zene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxy-benzene, 5-methyl-2-(1-methylethyl)phenol, 3-[(2-hydroxyethyl)amino]aniline, 3-[(2-amino-ethyl)amino]aniline, 1,3-di(2,4-diaminophe-noxy)propane, di(2,4-diaminophenoxy)methane, 1,3-di-amino-2,4-dimethoxybenzene, 2,6-bis(2-hydroxyethyl)ami-notoluene, 4-hydroxyin-dole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methyl-phenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxy-ethyl)amino]phenol, 3-[(2-meth-oxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypy-ridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihy-droxybenzene, 1-chloro-2,4-dihydroxybenzene, 2-chloro-1,3-dihydroxy-benzene, 1,2-di-chloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylene-dioxyaniline, 5-[(2-hydro-xyethyl)amino]-1,3-benzodiox-ole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydrox-yindoline, 5-hydroxyindole, 6-hydroxyindole, 7-hydroxyindole and 2,3-indolinedione.

In addition, the colorant of the invention can also contain direct anionic, cationic or neutral dyes. The preferred anionic dyes are, for example, disodium 6-hydroxy-5-[(4-sulfophenyl)azo]-2-naphthalenesulfonate (C.I. 15985; Food Yellow No. 3; FD&C Yellow No. 6), disodium 2,4-dinitro-1-naphthol-7-sulfonate (C.I. 10316; Acid Yellow No. 1; Food Yellow No. 1), 2-(indan-1,3-dion-2-yl)quinoline-x,x-sulfonic acid (mixture of mono- and disulfonic acid) (C.I. 47005; D&C Yellow No. 10, Food Yellow No.13, Acid Yellow No. 3), trisodium 5-hydroxy-1-(4-sulfophenyl)-4-[(4-sulfophenyl)azo]pyrazole-3-carboxylate (C.I. 19140; Food Yellow No. 4; Acid Yellow No. 23), 9-(2-carboxyphenyl)-6-hydroxy-3H-xanthen-3-one (C.I. 45350, Acid Yellow No. 73; D&C Yellow No. 8), monosodium 5-[(2,4-dinitrophenyl)amino]-2-phenylaminobenzenesulfonate (C.I. 10385; Acid Orange No. 3), monosodium 4-[(2,4-dihydroxyphenyl)azo]benzenesulfonate (C.I. 14270; Acid Orange No. 6), sodium 4-[(2-hydroxynaphth-1-yl)azo]benzenesulfonate (C.I. 15510; Acid Orange No. 7), sodium 4-[(2,4-dihydroxy-3-[(2,4-dimethylphenyl)azo]benzenesulfonate (C.I. 20170; Acid Orange No. 24), disodium 4-hydroxy-3-[(4-sulfonaphth-1-yl)azo]-1-naphthalenesulfonate (C.I. 14720; Acid Red No. 14), trisodium 6-hydroxy-5-[(4-sulfonaphth-1-yl)azo]-2,4-naphthalenedisulfonate (C.I. 16255; Ponceau 4R; Acid Red No. 18), trisodium 3-hydroxy-4-[(4-sulfonaphth-1-yl)azo]-2,7-naphthalenedisulfonate (C.I. 16185; Acid Red No. 27), disodium 8-amino-1-hydroxy-2-(phenylazo)-3,6-naphthalenedisulfonate (C.I. 17200; Acid Red No. 33), disodium 5-(acetylamino)-4-hydroxy-3-[(2-methyl-phenyl)azo]-2,7-naphthalenedisulfonate (C.I. 18065 Acid Red No. 35), disodium 2-(3-hydroxy-2,4,5,7-tetraaiododibenzopyran-6-on-9-yl)ben-zoate (C.I. 45430 Acid Red No. 51), N-[6-(diethylamino)-9-(2,4-disulfophenyl)-3H-xanthen-3-ylidene]-N-ethylethanaminium hydroxide, inner salt, sodium salt (C.I. 45100; Acid Red No. 52), disodium 8-[(4-(phenylazo)phenyl)azo]-7-naphthol-1,3-disulfonate (C.I. 27290; Acid Red No. 73), 2',4',5',7'-tetrabromo-3'-6'-dihydroxyspiro{isobenzofuran-1(3H),9'-[9H]xanthen]-3-one disodium salt (C.I. 45380; Acid Red No. 87), 2',4',5',7'-tetrabromo-4,5,6,7-tetrachloro-3',6'-dihydroxyspiro[isobenzofuran-1(3H),9'[9H]-3-one disodium salt (C.I. 45410; Acid Red No. 92), 3',6'-dihydroxy-4',5'-diiodospiro-[isobenzofuran1(3H),9'-(9H)-xanthen)-3-one disodium salt (C.I. 45425; Acid Red No. 95), (2-sulfophenyl)-di[4-(ethyl((4-sulfophenyl)methyl)amino)phenyl]carbenium disodium salt, betaine (C.I. 42090; Acid Blue No. 9; FD&C Blue No. 1), 4-bis[(2-sulfo-4-methylphenyl)amino]-9,10-anthraquinone disodium salt (C.I. 61570; Acid Green No. 25), bis[4-dimethylamino)phenyl]-3,7-disulfo-2-hydroxynaphth-1-yl)carbenium inner salt, monosodium salt (C.I. 44090; Food Green No. 4; Acid Green No. 50), bis[4-(diethylamino)phenyl](2,4-disulfophenyl)carbenium inner salt, sodium salt (2:1) (C.I. 42045; Food Blue No. 3; Acid Blue No. 1), bis[4-(diethyl-amino)phenyl](5-hydroxy-2,4-disulfophenyl)carbenium inner salt, calcium salt (2:1) (C.I. 42051; Acid Blue No. 3), sodium 1-amino-4-(cyclohexylamino)-9,10-anthraquinone-2-sulfonate (C.I. 62045; Acid Blue No. 62), disodium 2-(1,3-dihydro-3-keto-5-sulfo-2H-indol-2-ylidene)-2,3-dihydro-3-keto-1H-indole-5-sulfonate (C.I. 73015); Acid Blue No. 74), 9-(2-car-boxyphenyl)-3-[(2-methylphenyl)amino]-6-[(2-methyl-4-sulfophenyl)amino]xanthylium inner salt, monosodium salt (C.I. 45190; Acid Violet No. 9), sodium 1-hydroxy-4-[(4-methyl-2-sulfophenyl)amino]-9,10-anthraquinone (C.I. 60730; D&C Violet No. 2; Acid Violet No. 43), bis{3-nitro-4-[(4-phenylamino)-3-sulfophenylamino]phenyl} sulfone (C.I.10410; Acid Brown No. 13), disodium 5-amino-6-hydroxy-6-[(4-nitrophenyl)azo]-3-(phenylazo)-2,7-naphtha-lenedisulfonate (C.I.20470; Acid Black No. 1), 3-hydroxy-4-[(2-hydroxynaphth-1-yl)azo]-7-nitro-1-naphthalenesulfonic acid chromium complex (3:2) (C.I. 15711; Acid Black No. 52), disodium 3-[(2,4-dimethyl-5-sulfophenyl)azo]-4-hydroxy-1-napthalenesulfonate (C.I. 14700; Food Red No. 1; Ponceau SX; FD&C Red No. 4), tetrasodium 4-(acetylamino)-5-hydroxy-6-[(7-sulfo-4-[(4-sulfophenyl)azo]-naphth-1-yl)azo]-1,7-naphthalenedisulfonate (C.I. 28440; Food Black No.1) and sodium 3-hydroxy-4-(3-methyl-5-keto-1-phenyl-4,5-dihydro-1H-pyrazol-4-ylazo)naphthalenesulfonate chromium complex (Acid Red No.195).

For better color balancing and to create special color shades, the following nonionic dyes have been found to be particularly effective: 1-amino-2-[(2-hydroxyethyl)amino]-5-nitrobenzene (HC Yellow No. 5), 1-(2-hydroxyethoxy)-2-([(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxy-propoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yel-low No. 9), 1-[(2-ureidoethyl)amino]-4-nitrobenzene, 4-[(2,3-dihydroxypropyl)amino]-3-nitro-1-trifluoromethylbenzene, (HC Yellow No. 6), 1-chloro-2,4-bis-[(2-hydroxyethyl)amino]-5-nitrobenzene, 4-(2,3-dihydroxy-propoxy)-1-[(2-hydroxyethyl)amino]-2-nitrobenzene (HC Orange No. 3) (HC Yel-low No. 10), 4-[(2-hydroxyethyl)amino]-3-nitro-1-methylbenzene, 1-chloro-4-[(2-hydroxyethyl)-amino]-3-nitrobenzene (HC Yellow No. 12), 4-[(2-hydroxyethyl)-amino]-3-nitro-1-trifluoromethylbenzene (HC Yellow No. 13), 4-[2-hydroxyethyl)amino]-3-nitrobenzonitrile (HC Yel-low No. 14), 4-[(2-hydroxyethyl)amino]-3-nitrobenzamide (HC Yellow No. 15), 1-amino-4-[(2-hydroxyethyl)amino]-2-nitrobenzene (HC Red No. 7), 2-amino-4,6-dinitrophenol, 2-ethylamino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypro-pyl)amino]-2-nitrobenzene (HC Red No. 10), 5-chloro-1,4-[di(2,3-dihydroxypropyl)-amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-methylamino-4-nitrophenol, 2-chloro-6-[(2-hydroxyethyl)amino]-4-nitrophenol, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1,4-bis-(2-hydroxyethyl)amino-2-nitrobenzene, 1-(2-hydroxyethyl)amino-2-ni-tro-4-[(di(2-hydro-xyethyl)amino]benzene (HC Blue No. 2), 1-amino-3-methyl-4-[(2-hydroxy-ethyl)amino]-6-nitrobenzene (HC Violet No. 1), 4-[ethyl-(2-hydroxyethyl)amino]-1-[(2-hydroxyethyl)

amino]-2-nitrobenzene hydrochloride (HC Blue No. 12), 4-[di(2-hydroxyethyl)-amino]-1-[(2-methoxyethyl)amino]-2-nitrobenzene (HC Blue No. 11), 1-[(2,3-dihydroxy-propyl)amino]-4-[methyl-(2-hydroxyethyl)amino]-2-nitrobenzene (HC Blue No.10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl) amino]-2-nitrobenzene (HC Blue No. 6), 2-[(4-amino-2-nitrophenyl)amino]-5-dimethylaminobenzoic acid (HC Blue No. 13), 1,4-di[(2,3-dihydroxypropyl)amino]-9,10-anthraquinone C.I. 61505, Disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylami-no-9,10-anthraquinone (HC Blue No.8), 1-[(3-aminopropyl) amino]-9,10-anthraquinone (HC Red No. 8), 1,4-diamino-2-methoxy-9,10-anthraquinone (C.I. 62015, Disperse Red No. 11, Solvent Violet No. 26), 1-4-dihydroxy-5,8-bis-[(2-hydroxyethyl)amino]-9,10-anthraquinone (C.I. 62500, Disperse Blue No. 7, Solvent Blue No. 69), 1-[di(2-hydroxyethyl)amino]-3-methyl-4-[(4-nitrophenyl)azo]benzene (C.I. 11210, Disperse Red No. 17), 4-[(4-aminophenyl)azo]-1-[di (2-hydroxyethyl)amino]-3-methylbenzene (HC Yellow No. 7), 2,6-diamino-3-[(pyridin-3-yl)azo]pyridine and 2-{[4-(acetylamino)phenyl]azo}-4-methylphenol (C.I. 11855; Disperse Yellow No. 3).

Particularly noteworthy from the group of direct dyes are also 2-amino-4,6-dinitrophenol, 2-ethylamino-4,6-dinitrophenol, 2-[(2-hydroxyethyl)amino]-4,6-dinitrophenol and dyes having the general formula (VI)

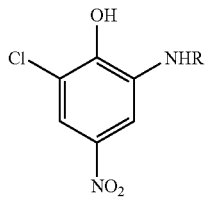

(VI)

wherein R denotes hydrogen, methyl, ethyl or hydroxyethyl.

The total concentration of developers and couplers in the ready-to-use colorant is preferably about 0.01 to 10 weight percent and particularly about 0.1 to 6 weight percent, whereas the total concentration of direct dyes amounts to 0.1 to 10 weight percent and particularly 0.1 to 5 weight percent.

In addition, the dye carrier composition can also contain antioxidants, perfume oils, complexing agents, wetting agents, emulsifiers, penetrants, buffer systems, preservatives, thickeners, hair-care agents and other cosmetic additives.

The dye carrier composition and the ready-to-use oxidation hair colorant can be prepared in the form of a solution, particularly an aqueous or aqueous-alcoholic solution. Particularly preferred preparation forms, however, are creams, gels or emulsions. They are composed of a mixture of dye components and additives commonly employed for such preparations.

Common additives to solutions, creams, emulsions or gels are, for example, solvents such as water, lower aliphatic alcohols, for example ethanol, n-propanol and isopropanol, or glycols such as glycerol and 1,2-propylene glycol, moreover wetting agents or emulsifiers from the classes of anionic, cationic, amphoteric or nonionic surface-active substances, such as fatty alcohol sulfates, ethoxylated fatty alcohol sulfates, alkylsulfonates, alkyl-benzenesulfonates, alkyltrimethylammonium salts, alkylbetaines, ethoxylated fatty alcohols, ethoxylated nonylphenols, fatty alkanolamides, ethoxylated fatty esters, furthermore thickeners such as the higher fatty alcohols, starch or cellulose derivatives, moreover vaselines, paraffin oils and fatty acids, as well as hair-care agents such as cationic resins, lanolin derivatives, cholesterol, pantothenic acid and betaine. The said constituents are used in amounts normally employed for such purposes. Based on the dye carrier composition, the wetting agents and emulsifiers, for example, are used at a concentration from about 0.5 to 30 weight percent, the thickeners in an amount from about 0.1 to 25 wt. % t and the hair-care agents at a concentration from about 0.1 to 5 wt. %.

The ready-to-use colorant of the invention is prepared just before use by mixing the dye carrier composition with an appropriate oxidant. In principle, it is also possible to carry out the oxidation with air, with or without enzymatic support.

The oxidants used are primarily hydrogen peroxide or the addition compounds thereof to urea, melamine or sodium bromate, in the form of a 1 to 12%, preferably 6% aqueous solution, hydrogen peroxide being particularly preferred.

The dye carrier composition and the oxidant are mixed with one another in a weight ratio from about 5:1 to about 1:3, a weight ratio of 1:1 to 1:2 being particularly preferred.

After mixing the, preferably alkaline, dye carrier composition with the mostly acidic oxidant, the pH of the ready-to-use colorant of the invention assumes a value that depends on the amount of alkali in the dye carrier composition and the amount of acid in the oxidant and on the mixing ratio. The pH of the ready-to-use colorant is about 3 to 11 and preferably 6 to 10.5.

The pH of the dye carrier composition and of the oxidant can be adjusted to the desired value with dilute organic or inorganic acids, for example phosphoric acid, ascorbic acid and lactic acid, or with an alkaline agent such as monoethanolamine, triethanolamine, 2-amino-2-methyl-1-propanol, ammonia, sodium hydroxide, potassium hydroxide, an amino acid or tris(hydroxymethyl)aminomethane.

After the dye carrier composition has been mixed with the oxidant, a sufficient amount, generally about 60 to 200 grams, of the ready-to-use oxidation colorant is applied to the fibers.

The colorant of the invention is allowed to act on the fibers for about 10 to 45 minutes at about 15 to 50° C., preferably for 30 minutes at 40° C., after which the fibers are rinsed with water. Optionally, this rinsing is followed by washing with a shampoo and possibly with a dilute weak organic acid, for example citric acid or tartaric acid. The fibers are then dried.

The following examples will explain the subject matter in greater detail without limiting its scope to these examples.

EXAMPLES

Example 1

Preparation of 1,3-diamino-4-(2-phenylethyl)benzene dihydrochloride 0.4 g of 2,4-dinitro-1-[(E)-2-phenylethenyl]benzene, prepared as described by S. B. Lokhande and D. W. Rangnekar, Ind. J. Chem. 25B, pages 485-488 (1986), was dissolved in 40 mL of ethanol, 50 mg of Pd/C 10% was added and the mixture was hydrogenated for 4 hours at 9 bar of hydrogen pressure. The catalyst was then removed by filtration through diatomite, and to the filtrate was added 10 mL of 1.8-molar alcoholic hydrochloric acid. By adding ethyl acetate as crystallization progressed, 0.38 g of product with a melting point of >250° C. (decomp.) was obtained.

FAB-MS 213 [M+H]$^+$

Example 2

Preparation of 1,3-diamino-4-[2-(4-methylphenyl)ethyl]benzene 1.4 g of 1,3-dinitro-4-[2-(4-methylphenyl)ethenyl]benzene prepared as described by S. Saravanan and P. Srinivasan, Synth. Commun. 31(6), pages 823-826 (2001) was dissolved in 50 mL of ethanol and hydrogenated using 0.2 g of Pd/C 10% for 4 hours at 8 bar of hydrogen pressure. The catalyst was then filtered off, and the filtrate was evaporated to dryness. This gave a brownish oil which upon addition of 10 mL of ether crystallized. Yield: 1.1 g of yellowish oil.

$^1$H-NMR (DMSO-d$_6$): δ=7.15 ppm (d, $^3J_{HH}$=7.8 Hz, 2H); 7.08 ppm (d, $^3J_{HH}$=7.8 Hz, 2H); 6.57 ppm (d, $^3J_{HH}$=7.9 Hz, 1H); 5.91 ppm (d, $^4J_{HH}$=2.1 Hz, 1H); 5.79 ppm (dd, $^3J_{HH}$=7.9 Hz, $^4J_{HH}$=2.1 Hz, 1H); 4.51 ppm (s broad, 4H); 2.65 ppm (m, 2H); 2.55 ppm (m, 2H), 2.27 ppm (s, 3H).

Example 3

Preparation of 1,3-diamino-4-[2-(4-methoxyphenyl)ethyl]benzene dihydrochloride 2.86 g of 1,3-dinitro-4-[2-(4-hydroxyphenyl)ethenyl]benzene, prepared as described by S. Saravanan and P. Srinivasan, Synth. Commun. 31(6), pages 823-826 (2001), in 50 mL of ethanol was hydrogenated using 0.3 g of Pd/C 10% for 2 hours at 8 bar of hydrogen pressure. The catalyst was then filtered off, and to the filtrate was added 30 mL of 1.8-molar ethanolic hydrochloric acid, after which the mixture was evaporated to dryness. This gave a brownish oil which after addition of 30 mL of ethyl acetate crystallized. Yield: 2.7 g of beige product.

$^1$H-NMR (DMSO-d$_6$): δ=9.33 ppm (s, very broad, 6H); 7.35-7.28 (signal overlap, 2H); 7.10 ppm (d, $^3J_{HH}$=8,3 Hz, 2H+signal overlap 1H); 6.70 ppm ($^3J_{HH}$=8.3 Hz, 2H); 2.85 ppm (m, 2H); 2.79 ppm (m, 2H).

Example 4

Preparation of 1,3-diamino-4-[2-(4-methoxyphenyl)ethyl]benzene

To 1 g of 1,3-diamino-4-[2-(4-methoxyphenyl)ethyl]benzene dihydrochloride from Example 3 in 50 mL of water was added saturated sodium carbonate solution to pH 8. The mixture was suction-filtered and the filter cake was washed with a small amount of cold water and then dried under vacuum over phosphorus pentoxide.

Yield: 0.8 of beige product, melting point: 187-189° C.

$^1$H-NMR (DMSO-d$_6$): δ=9.10 ppm (s, 1H); 7.05 ppm (d, $^3J_{HH}$=8.4 Hz, 2H); 6.67 ppm (d, $^3J_{HH}$=8.4 Hz, 2H); 6.57 ppm (d,$^3J_{HH}$=8.0 Hz, 1H); 5.91 ppm (d, $^4J_{HH}$=2.1 Hz, 1H); 5.79 ppm (dd, $^3J_{HH}$=8.0 Hz, $^4J_{HH}$=2.1 Hz, 1H); 4.52 ppm (s broadened, 4H); 2.60 ppm (m, 2H); 2.00 ppm (m, 2H, signal overlap with DMSO).

Example 5

Preparation of 1,3-diamino-4-{2-[4-(dimethylamino)phenyl]ethyl}-benzene trihydrochloride 10.03 g of 4-{(E)-2-[2,4-dinitrophenyl]ethenyl}-N,N-dimethylaniline, prepared as described by B. G. Thiemann, S. R. Marder and J. W. Perry, Chem. Mater. 1990, 2, pages 690-695, was dissolved in 200 mL of ethanol and hydrogenated for 7 hours at 9 bar of hydrogen pressure and using 1 g of Pd/C 10%. The catalyst was then removed by filtration through diatomite, and to the filtrate was added 200 mL of 3-molar ethanolic hydrochloric acid. The resulting solution was concentrated to 20% of its volume and 600 mL of ethyl acetate was added with agitation. This caused the product to crystallize. Recrystallization from 100 mL of 32% hydrochloric acid gave after drying under vacuum and over phosphorus pentoxide 8.4 g of colorless crystals which decomposed above 250° C.

$^1$H-NMR (DMSO-d$_6$): δ=7.68 ppm (d, $^3J_{HH}$=8.4 Hz, 2H); 7.52 ppm (d, $^3J_{HH}$=8.4 Hz, 2H); 7.27 ppm (d, $^3J_{HH}$=7.5 Hz, 1H); 7.12 ppm (s, broadened, 1H); 6.94 ppm (d broadened, $^3J_{HH}$=7.5 Hz, 1H); 3.10 ppm (s, 6H); 2.90 ppm (m, 4H).

FAB-MS: 256 [M+H$^+$], 100%

Elemental analysis: C$_{16}$H$_{21}$N$_3$, × 2.89 HCl × 0.79 H$_2$O: M = 374.97

|  | % C | % H | % N | % Cl |
|---|---|---|---|---|
| Calcd: | 51.25 | 6.85 | 11.21 | 27.32 |
| Found: | 51.23 | 6.46 | 11.26 | 27.31 |

Example 6

Preparation of 1,3-diamino-4-[2-(4-hydroxyphenyl)ethyl]benzene dihydrochloride Stage 1: 1-{(E)-2-[4-(benzyloxy)phenyl]ethenyl}-2,4-dinitrobenzene 18.21 g (0.1 mol) of 2,4-dinitrotoluene, 21.23 g (0.1 mol) of 4-benzyloxy-benzaldehyde and 1.8 mL of pyrrolidine in 140 mL of dimethylformamide were heated for 2 hours at 100° C. which caused the reaction mixture to assume a dark-brown color. The reaction mixture was then allowed to cool to room temperature after which it was diluted with 210 mL of isopropanol and allowed to agitate for an additional hour with ice cooling. The product was suction-filtered off, washed with a small amount of cold isopropanol and then dried at 40° C. under vacuum.

Yield: 21.4 g of orange-colored product (57% of the theoretical).

Elemental analysis: C$_{21}$H$_{16}$N$_2$O$_5$, M = 376.37

|  | % C | % H | % N |
|---|---|---|---|
| Calcd. | 67.02 | 4.29 | 7.44 |
| Found | 67.02 | 4.26 | 7.26 |

Stage 2:
1,3-Diamino-4-[2-(4-hydroxyphenyl)ethyl]benzene dihydrochloride 5.08 g (13.5 mmol) of the afore-described product was dissolved in 125 mL of ethanol, 500 mg of Pd/C 10% was added, and the mixture was subjected to hydrogenation for 4 hours at 9 bar of hydrogen pressure. The catalyst was then removed by filtration through diatomite. To the filtrate was added with agitation 3.7 g of 32% hydrochloric acid, and the mixture was concentrated to one-half its volume at 40° C. under reduced pressure, which caused crystallization to take place. The precipitated crude product was suction-filtered off and crystallized from a mixture of 15 mL of water and 5 mL of 32% hydrochloric acid. Suction-filtration and drying at 50° C. under vacuum afforded 5.4 g of beige product.

$^1$H-NMR (DMSO-d$_6$): δ=9.33 ppm (s, broad, OH and water); 7.31 ppm (d, $^3J_{HH}$=7.2 Hz, 2H); 7.11 ppm (m, 3H); 6.7 ppm (d, $^3J_{HH}$=8.2 Hz, 2H); 2.85 ppm (m, 2H).

Elemental analysis: C$_{14}$H$_{16}$N$_2$O × 2HCl (0.42% of residual moisture)
M = 302.48

|  | % C | % H | % N | % Cl |
|---|---|---|---|---|
| Calcd: | 55.59 | 6.04 | 9.26 | 23.44 |
| Found: | 55.80 | 6.00 | 9.30 | 23.20 |

Example 7

1,3-Diamino-4-[2-(4-pyridinyl)ethyl]benzene trihydrochloride

Stage 1:
4-[(E)-2-(2,4-dinitrophenyl)ethenyl]pyridine 1.4 g (7.7 mmol) of 2,4-dinitrotoluene, 0.82 g (7.7 mmol) of pyridine-4-carboxaldehyde and 0.2 mL of pyrrolidine were charged to a round-bottomed flask. The flask was fitted with a splash protector and then irradiated for 20 seconds in a domestic microwave oven (850 watt). The mixture was then allowed to cool, and the product was caused to precipitate by addition of 20 mL of acetone. Suction-filtration and drying at 40° C. under vacuum have 0.9 g of product (43% of the theoretical).

$^1$H-NMR (DMSO-d$_6$): δ=8.78 ppm (d, $^4J_{HH}$=2.2 Hz, 1H); 8.65 ppm (d, $^3J_{HH}$=6.0 Hz, 2H); 8.58 ppm (d, $^3J_{HH}$=8.6 Hz, $^4J_{HH}$=2.2 Hz, 1H); 8.27 ppm (d, $^3J$ HH=8.6 Hz, 1H); 8.27 ppm (d, $^3J_{HH}$=8.6 Hz, 1H); 7.81 ppm (d, $^3J_{HH}$=16.2 Hz, 1H); 7.64 ppm (d, $^3J_{HH}$=6.0 Hz); 7.54 ppm (d, $^3J_{HH}$=16.2 Hz,1H).

Stage 2:
1,3-Diamino-4-[2-(4-pyridinyl)ethyl]benzene trihydrochloride 0.3 g (1 mmol) of the product from Stage 1 in 20 mL of ethanol was hydrogenated for 4 hours using 50 mg of Pd/C 10% at 9 bar of hydrogen pressure. The catalyst was filtered off through diatomite, and 10 mL of a 3.3-molar ethanolic hydrochloric acid solution was added. To isolate the product, the mixture was thoroughly evaporated at 40° C. under reduced pressure, and the salt was caused to precipitate by addition of 10 to 15 mL of ethyl acetate. Suction filtration and drying under vacuum at 50° C. gave 0.28 g of beige product.

$^1$H-NMR (DMSO-d$_6$): δ=8.88 ppm (d, $^3J_{HH}$=6.5 Hz, 2H); 8.11 ppm (d, $^3J_{HH}$=6.5 Hz, 2H); 7.25 ppm (d, $^3J_{HH}$=8.0 Hz, 1H); 7.09 ppm (s, broadened, 1H); 6.92 ppm (d, broadened, $^3J_{HH}$=8.0 Hz, 1H); 3.24 ppm (m, 2H); 3.00 ppm (m, 2H).

Example 8

1,3-Diamino-4-[2-(3-pyridinyl)ethyl]benzene trihydrochloride

In analogy to the synthesis described in the preceding Example 7, pyridine-3-carboxaldehyde gave the corresponding 1,3-diamino-4-[2-(3-pyridinyl)ethyl]benzene trihydrochlo-ride in an overall yield of 48%.

$^1$H-NMR (DMSO-d$_6$): δ=9.04 ppm (s, 1H); 8.83 ppm (d, $^3J_{HH}$=5.4 Hz, 1H); 8.69 ppm (d, $^3J_{HH}$=8.1 Hz, 1H); 8.07 ppm (dd, $^4J_{HH}$=5.4 Hz, $^3J_{HH}$=8.1 Hz, 1H); 7.39 ppm (d, $^3J_{HH}$=8.0 Hz, 1H); 7.33 ppm (s, 1H); 7.15 ppm (d, $^3J_{HH}$=8.0 Hz, 1H); 3.20 ppm (m, 2H); 3.04 ppm (m, 2H).

Elemental analysis: C$_{13}$H$_{15}$N$_3$ × HCl (0.89% of residual moisture)
M = 325.55

|  | % C | % H | % N | % Cl |
|---|---|---|---|---|
| Calcd. | 47.96 | 5.67 | 12.91 | 32.67 |
| Found | 47.60 | 5.20 | 12.90 | 32.50 |

Example 9

Oxidation Hair Colorant, Basic Solution 0.25 mmol of the couplers of the invention of general formula (I) indicated in Table 1 was dissolved in 10 mL of the base formulation given hereinbelow.

| Base Formulation | |
|---|---|
| 80.00 g | of ethanol |
| 100.00 g | of sodium lauryl ether sulfate, 28% aqueous solution |
| 90.00 g | of ammonia, 25% aqueous solution |
| 3.00 g | of ascorbic acid |
| 4.00 g | of sodium sulfite |
| to 1000.00 g | water, demineralized |

In the same manner, 0.25 mmol of the developers indicated in Table 1 was dissolved in 10 mL of the base formulation.

Immediately before use, 10 g of the developer solution was mixed with 10 g of the coupler solution. To this mixture was then added 20 g of a 6% hydrogen peroxide solution which after mixing produced the ready-to-use colorant solutions. The ready-to-use oxidation hair colorants thus obtained were then applied to bleached hair. After an exposure time of 30 min at 40° C., the hair strands were rinsed, washed with a color-sparing shampoo and dried.

The resulting colorations were subjected to measurements in a Minolta Chromameter CR-300 by use of the L*a*b* system wherein L* stands for brightness, +a* for red content, −a* for green content, +b* for yellow content and −b* for blue content.

In the tables [see end of text], the ΔE values denote color changes in the L*a*b* system and are calculated by the equation $$\Delta E = \sqrt{(L_i - L_0)^2 + (a_i - a_0)^2 + (b_i - b_0)^2}$$

In this equation, $L_0$, $a_0$ and $b_0$ denote the measured values and $L_i$, $a_i$ and $b_i$ are the corresponding values obtained after the washing tests (note: the higher the calculated ΔE value, the higher is the color loss or color change).

The compounds of the invention of formula (I) are capable of giving with p-phenylenediamines very pure steel-blue colorations having a very high red content. In the L*a*b* analysis this is indicated by very low +a* values and by high values of −b*. The L*a*b* values are collected in Table 1.

TABLE 1

| Developer | 1,4-Diamino-2-methylbenzene sulfate (1:1) | 1,4-Diamino-2-(2-hydroxyethyl)-benzene sulfate (1:1) | 4-Amino-3-methylphenol | 4,5-Diamino-1-(2-hydroxyethyl)-1H-pyrazole sulfate (1:1) | 4-[Di(2-hydroxyethyl)amino]-aniline sulfate (1:1) |
|---|---|---|---|---|---|
| Coupler | | | | | |
| 2,4-Diamino-1-(2'-hydroxy-ethoxy)-benzene [Control] | L = 21.68<br>a = 4.88<br>b = −12.99 | L = 21.72<br>a = 6.28<br>b = −16.51 | L = 44.73<br>a = 17.91<br>b = 3.90 | L = 23.48<br>a = 37.90<br>b = 7.18 | L = 22.47<br>a = 4.29<br>b = −22.26 |
| 1b | L = 22.03<br>a = 5.75<br>b = −21.91 | L = 25.00<br>a = 5.10<br>b = −24.69 | L = 59.60<br>a = 13.03<br>b = −4.43 | L = 25.00<br>a = 40.51<br>b = −12.28 | — |
| 1g | L = 28.57<br>a = 2.92<br>b = −22.58 | L = 32.50<br>a = 2.80<br>b = −23.33 | L = 66.71<br>a = 7.52<br>b = 1.39 | L = 34.09<br>a = 43.50<br>b = −10.62 | L = 33.26<br>a = −2.41<br>b = −24.29 |
| 1d | L = 26.60<br>a = 0.03<br>b = −15.98 | L = 31.62<br>a = 0.43<br>b = −19.48 | L = 62.35<br>a = 7.29<br>b = 1.76 | L = 28.61<br>a = 37.74<br>b = −11.98 | L = 26.68<br>a = −3.56<br>b = −16.76 |
| 1h | L = 22.12<br>a = 2.62<br>b = −16.80 | L = 24.99<br>a = 3.81<br>b = −22.88 | L = 53.89<br>a = 3.06<br>b = −3.49 | L = 24.72<br>a = 38.28<br>b = −8.78 | L = 27.32<br>a = 0.14<br>b = −25.20 |
| 1e | L = 21.92<br>a = 6.45<br>b = −23.49 | L = 26.36<br>a = 4.70<br>b = −22.85 | L = 58.86<br>a = 10.47<br>b = −2.20 | L = 20.02<br>a = 41.12<br>b = −9.21 | L = 26.46<br>a = 0.74<br>b = −25.38 |
| 1i | L = 23.79<br>a = 5.45<br>b = −24.91 | L = 24.50<br>a = 5.01<br>b = −23.66 | L = 59.04<br>a = 10.19<br>b = 1.42 | L = 22.31<br>a = 38.08<br>b = −8.13 | L = 27.42<br>a = 1.06<br>b = −26.11 |
| 1k | L = 25.20<br>a = 4.31<br>b = −24.00 | L = 27.83<br>a = 4.71<br>b = −25.92 | L = 58.73<br>a = 4.72<br>b = −1.70 | L = 23.59<br>a = 37.59<br>b = −11.00 | L = 29.29<br>a = −3.08<br>b = −20.76 |
| 1v | L = 25.20<br>a = 4.31<br>b = −24.00 | L = 27.83<br>a = 4.71<br>b = −25.92 | L = 58.73<br>a = 4.72<br>b = −1.70 | L = 37.59<br>a = 37.59<br>b = −11.00 | L = 29.29<br>a = −3.08<br>b = −20.76 |
| 1a | L = 26.46<br>a = 5.11<br>b = −26.36 | L = 27.02<br>a = 4.34<br>b = −24.72 | L = 73.26<br>a = −0.28<br>b = 8.36 | L = 25.64<br>a = 38.97<br>b = −9.67 | L = 29.27<br>a = 1.12<br>b = −28.11 |
| 1d' | L = 29.11<br>a = 2.15<br>b = −22.47 | L = 29.82<br>a = 2.62<br>b = −23.89 | L = 65.71<br>a = 1.91<br>b = −0.34 | L = 27.26<br>a = 38.87<br>b = −14.47 | L = 29.22<br>a = −0.62<br>b = −25.21 |
| 1q | L = 24.33<br>a = 4.91<br>b = −24.38 | L = 27.23<br>a = 3.41<br>b = −23.93 | L = 63.91<br>a = 0.59<br>b = −0.15 | L = 23.85<br>a = 36.41<br>b = −13.85 | L = 27.74<br>a = 0.85<br>b = −26.02 |
| 1l | L = 54.12<br>a = −2.01<br>b = −1.76 | L = 56.91<br>a = −1.15<br>b = −1.36 | L = 82.60<br>a = 1.92<br>b = 12.12 | L = 50.29<br>a = 29.30<br>b = −6.24 | L = 49.59<br>a = −6.65<br>b = −8.27 |
| 1m | L = 48.28<br>a = −2.77<br>b = −7.68 | L = 49.26<br>a = −1.98<br>b = −7.54 | L = 78.88<br>a = 4.03<br>b = 7.72 | L = 47.11<br>a = 34.56<br>b = −7.95 | L = 46.24<br>a = −7.33<br>b = −11.39 |
| 1n | L = 24.51<br>a = 4.10<br>b = −23.11 | L = 25.38<br>a = 4.28<br>b = −23.95 | L = 57.89<br>a = 4.10<br>b = −3.42 | L = 24.82<br>a = 37.96<br>b = −11.46 | L = 27.64<br>a = −0.44<br>b = −23.88 |
| 1o | L = 31.04<br>a = 2.05<br>b = −23.32 | L = 31.58<br>a = 3.21<br>b = −24.12 | L = 67.72<br>a = 6.56<br>b = 0.47 | L = 30.01<br>a = 43.21<br>b = −8.82 | L = 32.42<br>a = −2.94<br>b = −25.13 |
| 1p | L = 23.90<br>a = 5.17<br>b = −24.35 | L = 24.91<br>a = 6.00<br>b = −26.23 | L = 72.31<br>a = 7.76<br>b = 8.77 | L = 29.90<br>a = 43.20<br>b = 13.71 | L = 33.40<br>a = −2.36<br>b = −27.17 |
| 1s | L = 43.51<br>a = −0.91<br>b = −5.06 | L = 49.73<br>a = −2.18<br>b = −2.52 | L = 77.54<br>a = 2.63<br>b = 9.10 | L = 45.77<br>a = 30.98<br>b = −6.44 | L = 46.05<br>a = −8.49<br>b = −3.19 |
| 1r | L = 0.33<br>a = −2.86<br>b = −1.19 | L = 42.24<br>a = −2.66<br>b = −8.26 | L = 72.40<br>a = 1.53<br>b = 5.37 | L = 40.15<br>a = 35.05<br>b = −8.12 | L = 40.09<br>a = −8.78<br>b = −9.23 |
| 1t | L = 24.85<br>a = 0.87<br>b = −15.51 | L = 26.89<br>a = 2.45<br>b = −19.78 | L = 58.62<br>a = 6.77<br>b = −2.73 | L = 25.46<br>a = 38.82<br>b = −10.57 | L = 29.12<br>a = −2.05<br>b = −21.51 |

TABLE 1-continued

| Developer | 1,4-Diamino-2-methylbenzene sulfate (1:1) | 1,4-Diamino-2-(2-hydroxyethyl)-benzene sulfate (1:1) | 4-Amino-3-methylphenol | 4,5-Diamino-1-(2-hydroxyethyl)-1H-pyrazole sulfate (1:1) | 4-[Di(2-hydroxyethyl)amino]-aniline sulfate (1:1) |
|---|---|---|---|---|---|
| 1u | L = 44.71<br>a = −1.61<br>b = 1.29 | L = 48.76<br>a = −1.73<br>b = 4.89 | L = 74.48<br>a = 1.72<br>b = 7.50 | L = 74.03<br>a = 1.20<br>b = −7.52 | L = 40.77<br>a = −6.60<br>b = −6.63 |
| 1f | L = 39.76<br>a = −2.40<br>b = −7.08 | L = 41.28<br>a = −1.68<br>b = −12.76 | L = 68.65<br>a = 7.25<br>b = 2.68 | L = 40.29<br>a = 40.36<br>b = −8.09 | L = 37.57<br>a = −6.89<br>b = −12.46 |
| 1c | L = 25.82<br>a = −0.10<br>b = −16.22 | L = 30.90<br>a = 1.80<br>b = −22.58 | L = 67.13<br>a = 5.85<br>b = 4.74 | L = 43.78<br>a = 33.22<br>b = −8.04 | L = 45.19<br>a = −6.25<br>b = −21.11 |

Example 10

Oxidation Hair Colorant, Basic Cream

| | |
|---|---|
| 15.00 g | of cetylstearyl alcohol |
| 5.00 g | of glycerol monostearate |
| 2.00 g | of cocamide DEA |
| 10.00 g | of sodium lauryl ether sulfate, 28% aqueous solution |
| 0.30 g | of ascorbic acid |
| 0.40 g | of sodium sulfite |
| 4.50 g | of ammonia, 25% aqueous solution |
| 0.25 mmol | of developer as per Table 2 |
| 0.25 mmol | of coupler as per Table 2 |
| to 100.00 g | water, demineralized |

The pH of the cream was between 10 and 10.5.

Just before use, the cream was mixed with 100 grams of a 6% aqueous hydrogen peroxide solution and the required amount of the resulting ready-to-use oxidation hair colorant was applied to bleached hair. The pH of the ready-to-use mixtures was between 9.5 and 10. After an exposure time of 30 minutes at 40° C., the hair was washed with a color-sparing shampoo, rinsed and dried.

The color shades obtained and the color intensities are collected in Table 2.

Example 11

Wash Resistance

Dyed hair strands from Example 10 were shampooed five times for 1 minute, dried and after final drying again subjected to measurement in the L*a*b* system. The differences in L*a*b* values and the ΔE values derived therefrom are collected in Tables 3a to 3c.

As the ΔE values indicate, the differences after the washing and drying cycles are in the range of measurement tolerances and visually are practically not discernible.

TABLE 3a

| Coupler | | 1,4-Diamino-2-methylbenzene sulfate (1:1) | | | |
|---|---|---|---|---|---|
| 1a | Developer | L | a | b | ΔE |
| | dyed | 17.0 | 3.6 | −11.7 | |
| | washed | 17.2 | 3.2 | −11.3 | 0.6 |

TABLE 3b

| Coupler | | 4-Amino-3-methylphenol | | | |
|---|---|---|---|---|---|
| 1g | Developer | L | a | b | ΔE |
| | dyed | 44.8 | 6.1 | −7.1 | |
| | washed | 47.3 | 6.0 | −5.4 | 3.0 |

TABLE 2

Coloring Results Obtained with the Cream Formulation

| Coupler | Developer | 1,4-Diamino-2-methylbenzene sulfate (1:1) | 1,4-Diamino-2-(2-hydroxyethyl)-benzene sulfate 1:1) | 4-Amino-3-methylphenol | 4,5-Diamino-1-(2-hydroxyethyl)-1H-pyrazole sulfate (1:1) | 4--[Di(2-hydroxyethyl)amino]-aniline sulfate (1:1) |
|---|---|---|---|---|---|---|
| 1a | | L = 17.0<br>a = 3.6<br>b = −11.7<br>dark blue | L = 18.0<br>a = 4.8<br>b = −15.7<br>dark blue | L = 37.4<br>a = 7.3<br>n = −10.6<br>pink | L = 18.4<br>a = 24.1<br>b = −5.9<br>brilliant violet | L = 20.2<br>a = 2.8<br>b = −18.2<br>dark steel-blue |
| 1g | | L = 18.1<br>a = 3.9<br>b = −14.9<br>dark blue | L = 20.3<br>a = 4.1<br>b = −17.1<br>dark blue | L = 44.8<br>a = 6.1<br>b = −7.1<br>pink | L = 19.2<br>a = 29.1<br>b = −5.9<br>brilliant violet | L = 19.7<br>a = 2.2<br>b = −17.1<br>dark steel-blue |
| 1e | | L = 21.6<br>a = −0.2<br>b = −12.1<br>dark blue | L = 20.9<br>a = 2.9<br>b = −16.5<br>dark blue | L = 49.9<br>a = 7.5<br>b = −5.0<br>bright pink | L = 20.4<br>a = 32.5<br>b = −7.6<br>brilliant violet | L = 21.3<br>a = −0.8<br>b = −14.9<br>dark cyan |

TABLE 3c

| Coupler 1e | Developer | 4,5-Diamino-1-(2-hydroxyethyl)-1H-pyrazole sulfate (1:1) | | | |
|---|---|---|---|---|---|
| | | L | a | b | ΔE |
| | dyed | 20.4 | 32.5 | −7.6 | |
| | washed | 20.9 | 32.4 | −9.1 | 1.6 |

Example 12

Oxidation Hair Colorant with Direct Dyes (Basic)

| | |
|---|---|
| 32.20 g | of cetylstearyl alcohol + Ceteareth 20 |
| 10.12 g | of glycerol stearate, vegetable origin (Tegin TB, supplied by Th. Goldschmidt) |
| 3.68 g | of lanolin alcohol |
| 4.00 g | of ethylene glycol distearate |
| 5.60 g | of sodium lauryl ether sulfate |
| 0.92 g | of sodium cocoylisethionate |
| 0.20 g | of ethylenediaminetetraacetate |
| 0.60 g | of ascorbic acid |
| 0.80 g | of sodium sulfite |
| 0.38 g | of 1,4-diamino-2-methylbenzene sulfate (1:1) |
| 0.66 g | of 1,4-diamino-2-(2-hydroxyethyl)benzene sulfate (1:1) |
| 0.46 g | of 4,5-diamino-1-(2-hydroxyethyl)-1H-pyrazole sulfate (1:1) |
| 0.54 g | of 4-amino-3-methylphenol |
| 0.54 g | of 1,3-diamino-4-(2-phenylethyl)benzene dihydrochloride (1a) |
| 0.26 g | of 1,3-diaminobenzene |
| 0.36 g | of 3-amino phenol |
| 0.42 g | of 5-amino-2-methylphenol |
| 0.60 g | of 2-chloro-6-(ethylamino)-4-nitrophenol |
| 9.00 g | of ammonia, 28% aqueous solution |
| to 200.00 g | water, demineralized |

The cream had a pH of 9.8.

Just before use, the cream was mixed with 100 g of a 6% or 9% aqueous hydrogen peroxide solution. The ready-to-use oxidation hair colorants thus obtained had a pH of 9.4 and 9.2, respectively. The ready-to-use hair colorants were applied to hair in an amount sufficient to achieve a coloration, and after an exposure time of 30 minutes at 40° C. were rinsed out. The hair was then washed with a color-sparing shampoo, rinsed and dried. The L*a*b* values and color shades are collected in Table 4.

TABLE 4

Colorations Obtained on Different Hair Types and With Different Hydrogen Peroxide Concentrations

| Hair Type | | Coloring Mixture I (hydrogen peroxide, 6%) | | | Coloring Mixture II (hydrogen peroxide, 9%) | | |
|---|---|---|---|---|---|---|---|
| | | L | a | b | L | a | b |
| Animal hair, bleached | not dyed | 82.5 | −0.2 | 11.0 | not dyed | 81.1 | −0.3 | 10.3 |
| | dyed | 17.6 | 3.4 | 2.6 | dyed | 18.5 | 3.9 | 3.1 |
| Human hair with 50% gray content | not dyed | 54.7 | 0.8 | 12.1 | not dyed | 58.9 | 0.2 | 12.3 |
| | dyed | 21.7 | 6.5 | 5.0 | dyed | 21.0 | 6.8 | 4.0 |
| Human hair, medium | not dyed | 31.6 | 5.9 | 11.2 | not dyed | 29.5 | 5.5 | 10.2 |

TABLE 4-continued

Colorations Obtained on Different Hair Types and With Different Hydrogen Peroxide Concentrations

| Hair Type | | Coloring Mixture I (hydrogen peroxide, 6%) | | | Coloring Mixture II (hydrogen peroxide, 9%) | | |
|---|---|---|---|---|---|---|---|
| | | L | a | b | L | a | b |
| blond, shade depth 7/0 | dyed | 20.7 | 5.1 | 3.8 | dyed | 20.1 | 5.1 | 4.0 |

All hairs were dyed to a dark eggplant shade. On human hair, which when not dyed had a 50% gray content, the gray parts were completely covered with a uniform coloration. No significant differences due to the use of the higher amount of hydrogen peroxide were ob-served.

Unless otherwise indicated, all percentages are by weight.

The invention claimed is:

1. A m-diaminobenzene compound of formula (I):

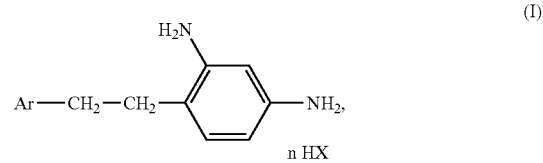

(I)

wherein
n is a number such that $0 \leq n \leq 3$,
HX stands for an organic or inorganic acid, and
Ar denotes a naphthyl group, a methylenedioxyphenyl group, a substituted or unsubstituted or benzo-condensed five- or six-membered heteroaromatic group, or a benzo-aromatic group of formula (II)

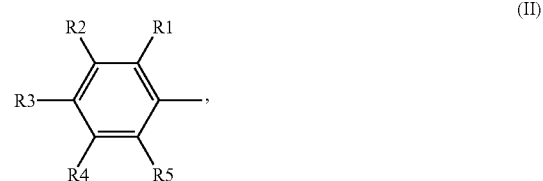

(II)

wherein R1 to R5, independently of each other, each denote a hydrogen atom, a halogen atom, a hydroxyl group, a nitrile group, a carboxamido group, an acetylamino group, a straight-chain or branched $C_1$-$C_{12}$-alkyl group, a straight-chain or branched $C_1$-$C_{12}$-alkoxy group, a straight-chain or branched $C_1$-$C_{12}$-alkylamino group, a straight-chain or branched di-($C_1$-$C_6$)-alkylamino group, a phenyl group, a morpholino group, a pyrrolidino group, a piperidino group, a piperazino group, a $C_2$-$C_4$-hydroxyalkyl group, a $C_2$-$C_4$-hydroxyalkoxy group, a benzyloxy group, a trifluoromethyl group, or a methylsulfonyl group; and with the proviso that Ar is not an imidazolyl group.

2. The m-diaminobenzene compound as defined in claim 1, wherein Ar denotes a pyridinyl group, a furyl group, a thienyl group, a pyrrol group, an indolyl group, or a pyrazolyl group.

3. A m-diaminobenzene compound selected from the group consisting of
1,3-diamino-4-(2-phenylethyl)benzene dihydrochloride,
1,3-diamino-4-[2-(4-methyl phenyl)ethyl]benzene,
1,3-diamino-4-[2-(1-naphthyl)ethyl]benzene dihydrochloride,
1,3-diamino-4-[2-(4-methoxyphenyl)ethyl]benzene,
1,3-diamino-4-[2-(4-hydroxyphenyl)ethyl]benzene dihydrochloride,
1,3-diamino-4-[2-(4-hydroxyphenyl)ethyl]benzene,
1,3-diamino-4-{2-[4-(dimethylamino)phenyl]ethyl}benzene trihydrochloride,
4-[2-(4-cyanophenyl)ethyl]-1,3-diaminobenzene dihydrochloride,
1,3-diamino-4-[2-(4-pyridinyl)ethyl]benzene trihydrochloride,
1,3-diamino-4-[2-(3-pyridinyl)ethyl]benzene trihydrochloride,
1,3-diamino-4-[2-(4-biphenyl)ethyl]benzene dihydrochloride,
1,3-diamino-4-[2-(2,4-dimethoxyphenyl)ethyl]benzene,
1,3-diamino-4-[2-(4-hydroxy-3-methoxyphenyl)ethyl]benzene,
1,3-diamino-4-[2-(3,4,5-trihydroxyphenyl)ethyl]benzene,
1,3-diamino-4-{2-[4-(2-hydroxyethoxy)phenyl]ethyl}-benzene,
1,3-diamino-4-[2-(2-thienyl)ethyl]benzene,
1,3-diamino-4-[2-(2-furyl)ethyl]benzene,
1,3-diamino-4-[2-(5-methyl-2-furyl)ethyl]benzene,
1,3-diamino-4-[2-(1H-indol-3-yl)ethyl]benzene,
1,3-diamino-4-[2-(1-methyl-1H-indol-3-yl)ethyl]benzene and
1,3-diamino-4-[2-(2-pyridinyl)ethyl]benzene trihydrochloride.

4. An agent for oxidative dyeing of fibers, said agent comprising a dye carrier composition and at least one m-diaminobenzene compound of formula I:

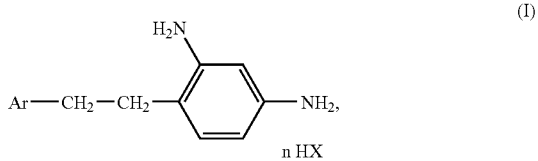

wherein
n is a number such that $0 \leq n \leq 3$,
HX stands for an organic or inorganic acid, and
Ar denotes a naphthyl group, a methylenedioxyphenyl group, a substituted or
unsubstituted or benzo-condensed five- or six-membered heteroaromatic group,
or a benzo-aromatic group of formula (II)

wherein R1 to R5, independently of each other, each denote a hydrogen atom, a halogen atom, a hydroxyl group, a nitrile group, a carboxamido group, an acetylamino group, a straight-chain or branched $C_1$-$C_{12}$-alkyl group, a straight-chain or branched $C_1$-$C_{12}$-alkoxy group, a straight-chain or branched $C_1$-$C_{12}$-alkylamino group, a straight-chain or branched di-($C_1$-$C_6$)-alkylamino group, a phenyl group, a morpholino group, a pyrrolidino group, a piperidino group, a piperazino group, a $C_2$-$C_4$-hydroxyalkyl group, a $C_2$-$C_4$-hydroxyalkoxy group, a benzyloxy group, a trifluoromethyl group, or a methylsulfonyl group; and with the proviso that Ar is not an imidazolyl group.

5. The agent as defined in claim 4, containing from 0.01 to 20 weight percent of said at least one m-diaminobenzene compound of the formula I.

6. The agent as defined in claim 4, further comprising a developer compound and/or a coupler compound and/or a direct dye compound, and wherein said coupler compound is not said at least one m-diaminobenzene of the formula I.

7. A ready-to-apply composition for oxidative dyeing of fibers, said ready-to-apply composition comprising a dye carrier composition, an oxidant, and at least one m-diaminobenzene compound of formula I:

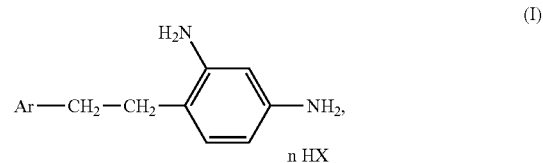

wherein
n is a number such that $0 \leq n \leq 3$,
HX stands for an organic or inorganic acid, and
Ar denotes a naphthyl group, a methylenedioxyphenyl group, a substituted or
unsubstituted or benzo-condensed five- or six-membered heteroaromatic group,
or a benzo-aromatic group of formula (II)

wherein R1 to R5, independently of each other, each denote a hydrogen atom, a halogen atom, a hydroxyl group, a nitrile group, a carboxamido group, an acetylamino group, a straight-chain or branched $C_1$-$C_{12}$-alkyl group, a straight-chain or branched $C_1$-$C_{12}$-alkoxy group, a straight-chain or branched $C_1$-$C_{12}$-alkylamino group, a straight-chain or branched di-($C_1$-$C_6$)-alkylamino group, a phenyl group, a morpholino group, a pyrrolidino group, a piperidino group, a piperazino group, a $C_2$-$C_4$-hydroxyalkyl group, a $C_2$-$C_4$-hydroxyalkoxy group, a benzyloxy group, a trifluoromethyl group, or a methylsulfonyl group; and with the proviso that Ar is not an imidazolyl group.

8. The ready-to-apply composition as defined in claim 7, wherein said oxidant is hydrogen peroxide.

9. The agent as defined in claim 4, consisting of a hair colorant.

10. A method of oxidatively dyeing fibers, said method comprising the steps of:
   a) applying a ready-to-apply composition for dyeing fibers to the fibers in an amount sufficient for the dyeing of the fibers;
   b) allowing the ready-to-apply composition to act on the hair for about 10 to 45 minutes at about 15° C. to 50° C. and then
   c) rinsing the ready-to-apply composition from the fibers;
   wherein said ready-to-apply composition comprises a dye carrier composition, an oxidant, and at least one m-diaminobenzene compound of formula I:

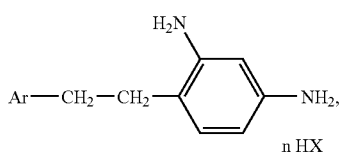

(I)

wherein n is a number such that $0 \leq n \leq 3$,

HX stands for an organic or inorganic acid, and

Ar denotes a naphthyl group, a methylenedioxyphenyl group, a substituted or unsubstituted or benzo-condensed five- or six-membered heteroaromatic group, or a benzo-aromatic group of formula (II)

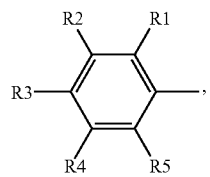

(II)

wherein R1 to R5, independently of each other, each denote a hydrogen atom, a halogen atom, a hydroxyl group, a nitrile group, a carboxamido group, an acetylamino group, a straight-chain or branched $C_1$-$C_{12}$-alkyl group, a straight-chain or branched $C_1$-$C_{12}$-alkoxy group, a straight-chain or branched $C_1$-$C_{12}$-alkylamino group, a straight-chain or branched di-($C_1$-$C_6$)-alkylamino group, a phenyl group, a morpholino group, a pyrrolidino group, a piperidino group, a piperazino group, a $C_2$-$C_4$-hydroxyalkyl group, a $C_2$-$C_4$-hydroxyalkoxy group, a benzyloxy group, a trifluoromethyl group, or a methylsulfonyl group; and with the proviso that Ar is not an imidazolyl group.

11. The method as defined in claim 10, wherein said oxidant is hydrogen peroxide or an addition compound of hydrogen peroxide to urea, melamine, or sodium bromate.

12. The method as defined in claim 10, wherein said oxidant is an aqueous solution of hydrogen peroxide containing from 1 to 12% of said hydrogen peroxide.

13. The method as defined in claim 12, wherein said dye carrier composition and said oxidant are mixed with one another in a weight ratio of from about 5:1 to 1:3 to form said ready-to-apply composition.

14. The method as defined in claim 10, wherein said ready-to-apply composition has a pH of 6 to 10.5.

* * * * *